US009452150B2

(12) United States Patent
Ueshima et al.

(10) Patent No.: US 9,452,150 B2
(45) Date of Patent: *Sep. 27, 2016

(54) JELLY COMPOSITION (75) Inventors: Hiroki Ueshima, Shizuoka (JP);
Shigeharu Suzuki, Shizuoka (JP);
Naomi Yokomizo, Shizuoka (JP);
Atsushi Sato, Shizuoka (JP); Hirosato Fujii, Shizuoka (JP)

(73) Assignee: MOCHIDA PHARMACEUTICAL CO., LTD., Tokyo (JP)

( * ) Notice: Subject to any disclaimer, the term of this patent is extended or adjusted under 35 U.S.C. 154(b) by 1431 days.

This patent is subject to a terminal disclaimer.

(21) Appl. No.: 11/660,359

(22) PCT Filed: Aug. 18, 2005

(86) PCT No.: PCT/JP2005/015079
§ 371 (c)(1),
(2), (4) Date: Feb. 16, 2007

(87) PCT Pub. No.: WO2006/019140
PCT Pub. Date: Feb. 23, 2006

(65) Prior Publication Data
US 2007/0259957 A1  Nov. 8, 2007

(30) Foreign Application Priority Data
Aug. 18, 2004  (JP) ................. 2004-238419

(51) Int. Cl.
A61K 31/19 (2006.01)
A61K 31/20 (2006.01)
A61K 47/00 (2006.01)
A61K 31/202 (2006.01)
A61K 9/06 (2006.01)
A61K 31/232 (2006.01)
A61K 47/12 (2006.01)
A61K 47/14 (2006.01)

(52) U.S. Cl.
CPC .............. *A61K 31/202* (2013.01); *A61K 9/06* (2013.01); *A61K 31/232* (2013.01); *A61K 47/12* (2013.01); *A61K 47/14* (2013.01)

(58) Field of Classification Search
CPC .... A61K 31/202; A61K 31/232; A61K 9/06; A61K 47/12; A61K 47/14
USPC ....... 514/553, 506, 715, 485, 557, 560, 724, 514/780
See application file for complete search history.

(56) References Cited

U.S. PATENT DOCUMENTS

| 5,932,235 A | 8/1999 | Ninomiya et al. |
| 6,458,395 B1 | 10/2002 | Emoto et al. |
| 2005/0147665 A1* | 7/2005 | Horrobin et al. ............. 424/456 |
| 2005/0175628 A1 | 8/2005 | Fukuchi et al. |

FOREIGN PATENT DOCUMENTS

| EP | 1046347 A1 | 10/2000 |
| EP | 1163905 A1 | 12/2001 |
| JP | 2-186953 A | 7/1990 |
| JP | 8-242786 A | 9/1996 |
| JP | 9-187233 A | 7/1997 |
| JP | 9-194346 A | 7/1997 |
| JP | 09-224578 A | 9/1997 |
| JP | 10-155433 A | 6/1998 |
| JP | 11-056245 A | 3/1999 |
| JP | 11-056315 A | 3/1999 |
| JP | 11-123231 A | 5/1999 |
| JP | 11-318356 A | 11/1999 |
| JP | 2001-114696 A | 4/2001 |
| JP | 2001-275620 A | 10/2001 |
| JP | 2002-354991 A | 12/2002 |
| JP | 2004-008165 A | 1/2004 |
| JP | 2004-059503 A | 2/2004 |

OTHER PUBLICATIONS

Extended European Search Report issued to corresponding European Application No. 05773735.5 dated May 7, 2012.
Hidehiko Hibino, "The Feature of the Physiology Function about Perilla Oil Which is Rich in alpha-Linolenicacid," (Food Research Laboratory, Nippon Oil & Fats, Co.), "Food Processing and Ingredients," vol. 38, No. 3, pp. 76-81, published by UBM Media Co. LTD Mar. 2003 with partial translation.
Office Action issued in corresponding Japanese Patent Application No. 2006-531854 dated May 24, 2011.

* cited by examiner

*Primary Examiner* — Shobha Kantamneni
(74) *Attorney, Agent, or Firm* — Birch, Stewart, Kolasch & Birch, LLP (57) ABSTRACT

A composition in which a preparation of the composition itself has an excellent disintegratability in the right place and excellent active ingredient releasability within the digestive tract, the active ingredient and the preparation itself have long-term stability, excellent ease of operation such as manufacturability and filling into containers, an amount sufficient for achieving physiological effects can be easily taken and swallowed, and can be absorbed rapidly from the digestive tract, thus the physiological effect can be expected. The composition is an easy-release jelly composition containing an emulsified polyvalent unsaturated fatty acid or derivative thereof in an amount exceedingly 10 mass % and further containing an emulsifying agent and a gallant. The easy-release jelly composition includes an emulsified polyunsaturated fatty acid or derivative thereof in an amount greater than 10 wt %, an emulsifying agent, and a gelling agent.

22 Claims, 1 Drawing Sheet

JELLY COMPOSITION

TECHNICAL FIELD

The present invention relates to an easy-release jelly composition having excellent properties such as easy oral taking and stability which contains a polyunsaturated fatty acid in an amount greater than 10 wt % that has been emulsified in a oil-in-water system, and relates more particularly to a pharmaceutical composition.

BACKGROUND ART

Polyunsaturated fatty acids are defined as fatty acids which have a plurality of carbon-carbon double bonds on the molecule, and are classified according to the positions of the double bonds as, for example, ω-3 polyunsaturated fatty acids or ω-6 polyunsaturated fatty acids. Examples of ω-3 polyunsaturated fatty acids include α-linolenic acid, eicosapentaenoic acid (EPA) and docosahexaenoic acid (DHA). Examples of ω-6 polyunsaturated fatty acids include linoleic acid, γ-linolenic acid and arachidonic acid. Because polyunsaturated fatty acids exhibit a variety of effects, such as antiatherogenic effects, platelet aggregation-inhibiting effects, blood lipid-lowering effects, anti-inflammatory effects, anticancer effects and central nervous system effects, they are formulated in various types of food products and are also sold commercially as health foods or pharmaceutical products. Polyunsaturated fatty acids readily oxidize. Because they emit a characteristic odor when they oxidize, such fatty acids are generally prepared in capsule form to prevent oxidation and block odors. For polyunsaturated fatty acids to exhibit effects such as those mentioned above, they must be taken in a dose of from several hundred milligrams to several grams at a time. Not only are the capsules large and difficult to swallow, a plurality of capsules must be ingested. These and other problems pose a challenge to the administration of polyunsaturated fatty acids. Such problems are particularly acute in the elderly and other patients who have difficulty swallowing. Moreover, in patients whose intake of water is restricted, large and/or numerous capsules must be ingested with a limited amount of water, which is highly unpleasant.

Also, in the elderly and other patients who have difficulty swallowing, it is not uncommon for food and drink to enter the trachea due to aspiration, causing pneumonia. Such aspiration is known to occur less readily with high-viscosity gels and jellies than with low-viscosity liquids such as water (Kuchi kara taberu enka-shōgai Q&A [Swallowing disorders when eating by mouth: Questions and Answers], by Ichiro FUJISHIMA (Chuohoki Publishers)). This has led recently to the development and marketing of jelly preparations as pharmaceuticals which can easily be taken even by patients having a lowered ability to swallow.

Prior-art jelly preparations include such marketed jelly preparations as Acivir Oral Jelly (manufactured by Ohta Pharmaceutical Co., Ltd./sold by Nikken Chemicals Co., Ltd.) which contains the antiviral agent aciclovir, Ciloslet Oral Jelly (manufactured by Ohta Pharmaceutical Co., Ltd./sold by Zeria Pharmaceutical Co., Ltd.) which contains the drug cilostazol used for treating chronic arterial occlusion, and Pabron Cough Medicine, an over-the-counter medication in stick jelly form (manufactured by Ohta Pharmaceutical Co., Ltd./sold by Taisho Pharmaceutical Co., Ltd.).

In addition, jelly compositions containing carrageenan, locust bean gum and polyacrylic acid which do not readily undergo syneresis and have an excellent storage stability (e.g., Patent Documents 1 and 2), and jelly-like compositions which are formulated with undiluted Chinese herbal medications, contain carrageenan, locust bean gum, xanthan gum and phosphate buffers, and have an excellent storage stability (e.g., Patent Document 3) have been disclosed.

Fatty acid-containing jelly-like compositions that have been disclosed include jelly-like candies composed of γ-linolenic acid-containing oils, gelling agents, water and sugars (e.g., Patent Document 4); jelly foods which contain at least powdered konjak and a gelling agent, additionally include 0.5 to 10.0 wt % of fats and oils, and have a smooth, tofu-like consistency with good mouth-melt characteristics (e.g., Patent Document 5); retort foods of fish and shellfish in which the seasoning broth contains κ-carrageenan and locust bean gum and has been jellied (e.g., Patent Document 6); and gel-like foods composed primarily of 1 to 10 wt % of medium-chain fatty acids, retarded blood sugar value delay-elevating carbohydrates, gelling agents and water (e.g., Patent Document 7).

However, in the prior art on these jelly-like compositions and jelly-like food products, no mention can be found of any investigations, disclosures or suggestions concerning the inclusion of polyunsaturated fatty acids in an amount greater than 10 wt % and the disintegrating ability, releasability and biological utility which are critical to pharmaceutical compositions. More specifically, in the prior art on such jelly compositions, no disclosure whatsoever is made concerning art relating to the release of oils and fats from such jelly compositions within the oral cavity or the digestive tract following administration, which is of particular importance for pharmaceutical compositions. Nor has any art been investigated based on a desire to increase the in vivo absorptivity of unsaturated fatty acids as active ingredients.

Moreover, to ingest at one time the 600 mg of EPA that is generally regarded as exhibiting a physiological effect by taking a jelly having an oil and fat content of 2 wt % according to the art described in Patent Document 5, for example, one would have to take about 30 g of the jelly. As noted above, in order for the polyunsaturated fatty acids to be efficiently absorbed in vivo, the jelly must be taken after a meal. However, in a patient who feels full after a meal, the requirement that a large amount of jelly be ingested will effectively lower compliance, preventing the required amount from being ingested. Furthermore, in elderly and other patients having a diminished ability to swallow and in patients whose intake of water is restricted, administration may be difficult if the amount of jelly that must be ingested to receive the effective dose of the active ingredient is large.

Patent Document 1: JP 9-187233 A
Patent Document 2: JP 9-194346 A
Patent Document 3: JP 2001-114696 A
Patent Document 4: JP 9-224578 A
Patent Document 5: JP 2002-354991 A
Patent Document 6: JP 2001-275620 A
Patent Document 7: JP 2004-8165 A

DISCLOSURE OF THE INVENTION

Problems to be Solved by the Invention

The object of the invention is to provide compositions, and a method of manufacture thereof, which have at least one of the following characteristics. That is, the object of the invention is to provide jelly compositions, particularly pharmaceutical compositions, which stably contain emulsified polyunsaturated fatty acids in an amount greater than 10 wt %, enabling the amount of the composition administered at one time to be decreased; which have an excellent ability to release the active ingredient within the digestive tract; which allow the active ingredient to be readily absorbed from the digestive tract; which are characterized in that the active ingredient and the preparation itself have long-term stability; which have, under controlled production conditions, an excellent ease of operation such as manufacturability and filling into containers; which do not disintegrate when carried and prior to ingestion; and which have excellent disintegratability following ingestion.

Means for Solving the Problems

As a result of extensive investigations aimed at resolving the above problems, the inventors have found that jelly compositions manufactured by adding an appropriate amount of a specific gelling agent to a oil-in-water emulsion, which is itself prepared by the addition of a suitable amount of a specific emulsifying agent to a polyunsaturated fatty acid, satisfy at least one of the above characteristics. This discovery ultimately led to the present invention.

Effects of the Invention

The jelly composition of the invention includes an emulsified polyunsaturated fatty acid in an amount greater than 10 wt % that is readily releasable. Moreover, this composition possesses at least one of the following characteristics: excellent portability, easy to take even by patients who have a reduced ability to swallow, can be easily administered without water even to patients whose intake of water is restricted (e.g., dialysis patients), the preparation itself has a suitable strength yet has an excellent disintegratability in the right place and excellent active ingredient releasability within the digestive tract, the active ingredient and the preparation itself have long-term stability, excellent ease of operation such as manufacturability and filling into containers under controlled production conditions, polyunsaturated fatty acids in an amount sufficient for achieving physiological effects can be easily taken and swallowed without experiencing any unpleasant taste or odor, and can be absorbed as rapidly from the digestive tract as the soft capsules hitherto used as the dosage form, thus the physiological effect can be expected.

BEST MODE FOR CARRYING OUT THE INVENTION

The invention is described more fully below.

Polyunsaturated fatty acids are defined as fatty acids having a plurality of carbon-carbon double bonds on the molecule, and are classified according to the position of the double bonds as, for example, ω-3 polyunsaturated fatty acids and ω-6 polyunsaturated fatty acids. Examples of ω-3 polyunsaturated fatty acids include α-linolenic acid, EPA and DHA. Examples of ω-6 polyunsaturated fatty acids include linoleic acid, γ-linolenic acid and arachidonic acid. The polyunsaturated fatty acids used in the invention may be synthetic products or natural products, or may be in the form of a natural oil containing these. Synthetic products include not only chemically synthesized products, but also semi-synthetic products obtained by subjecting a polyunsaturated fatty acid produced by microbes or the like as the starting material to esterification, transesterification or the like. "Natural products" refers herein to products extracted by a known method from a natural oil containing polyunsaturated fatty acid, crude products, and products obtained by the purification of these to an even higher degree. Salts, esters, amides, phospholipids, monoglycerides, diglycerides, triglycerides and other derivatives of polyunsaturated fatty acids are also encompassed by the polyunsaturated fatty acid employed in the invention.

The polyunsaturated fatty acid used in the invention is preferably an Ω-3 polyunsaturated fatty acid, more preferably at least one selected from among EPA, DHA and α-linolenic acid, even more preferably EPA, DHA or a mixture of both, still more preferably ethyl eicosapentaenoate (EPA-E), ethyl docosahexaenoate (DHA-E) or a mixture of both, and most preferably EPA-E. Preferred embodiments include jelly compositions in which the polyunsaturated fatty acid is a refined fish oil, and jelly compositions in which the polyunsaturated fatty acid is at least one selected from among monoglycerides, diglycerides and triglycerides.

The purity of the polyunsaturated fatty acid in the inventive composition, that is, the content of polyunsaturated fatty acid in the total fatty acids, while not subject to any particular limitation, is preferably at least 25 wt %, more preferably at least 50 wt %, even more preferably at least 70 wt %, still more preferably at least 85 wt %, and most preferably contains substantially no fatty acid components other than polyunsaturated fatty acids. As used herein, "contains substantially no fatty acid components other than polyunsaturated fatty acids" is a provision concerning fatty acids included as active ingredients; fatty acids included as the emulsifying agent or the like are not encompassed by the other fatty acid components referred to here.

The amount of polyunsaturated fatty acid used in the invention is an amount greater than 10 wt % of the jelly composition, preferably greater than 10 wt % but not more than 50 wt %, and more preferably greater than 15 wt % but not more than 30 wt %. This amount is suitably selected while taking into account, for example, the amount of jelly composition to be filled into the container and the purity of the polyunsaturated fatty acid.

If the jelly composition has an oil and fat content in excess of 10 wt, the amount of jelly administered can be greatly reduced. For example, at an oil and fat content of 20 wt %, the dose of jelly required to ingest 600 mg of EPA is 3 g. For the polyunsaturated fatty acid to be efficiently absorbed by the body, it is critical that the jelly be ingested after a meal. In such a case, the amount of jelly to be taken by the patient who feels full after a meal is a very important factor in patient compliance. Moreover, a smaller amount of jelly is easier to administer also in elderly and other patients having a reduced ability to swallow and in patients whose intake of water is restricted. Hence, the industrial utility can be increased by elevating the content of oil and fat included in the jelly.

As used herein, "easy release" indicates that the polyunsaturated fatty acid contained in the jelly composition is rapidly released and absorbed within the digestive tract when the jelly composition is administered. Referring to a method that is based on the paddle method for dissolution testing in the Pharmacopoeia of Japan (*International Journal of Pharmaceutics* 95, 67-75), "easy release" is defined as satisfying either case (1) or case (2) below: (1) when 200 mL of a sodium phosphate buffer (pH, 6.8; containing 20% of polysorbate 20) is used as the test solution, 2,500 polypropylene beads (diameter, 6.35 mm) are placed together with the test solution in a dissolution testing apparatus beaker, and testing is carried out by rotating the paddle at 25 rpm and a temperature of 37° C., at least 65% (percent release) of the polyunsaturated fatty acid is released into the test solution 30 minutes following the start of the test; and (2) cases in which, when 160 mL of an artificial gastric fluid (a solution prepared by adjusting an aqueous solution containing 115 mmol/L of sodium chloride and 35 mmol/L of potassium chloride to pH 2.5 with hydrochloric acid) is used as the test solution, 2,000 nylon beads (diameter, 6.4 mm) are placed together with the test solution in a dissolution testing apparatus beaker, and testing is carried out by rotating the paddle at 25 rpm and a temperature of 37° C., at least 50% (percent release) of the polyunsaturated fatty acid is released into the test solution 30 minutes following the start of the test.

In the practice of the invention, the emulsifying agent for emulsifying and dispersing the polyunsaturated fatty acid in a oil-in-water system is exemplified by sucrose fatty acid esters, glycerol fatty acid esters, polyglycerol fatty acid esters, lecithin, polyoxyethylene polyoxypropylene glycols, sorbitan fatty acid esters, propylene glycol fatty acid esters and $C_{12-22}$ saturated fatty acids. The emulsifying agent content is from 0.01 to 20 wt %, preferably from 0.05 to 10 wt %, and more preferably from 0.1 to 5 wt %. A single emulsifying agent may be used alone or a plurality of emulsifying agents may be used together in combination. When a single emulsifying agent is used alone, a polyoxyethylene polyoxypropylene glycol is preferred. The emulsifying agent content is preferably from 0.1 to 10 wt %. When a plurality of emulsifying agents are used in combination, it is preferable to combine a polyoxyethylene polyoxypropylene glycol with at least one selected from among sucrose fatty acid esters, lecithin, sorbitan fatty acid esters, propylene glycol fatty acid esters and $C_{12-22}$ saturated fatty acids. It is preferable to include from 0.1 to 10 wt % of each. The polyoxyethylene polyoxypropylene glycol is preferably one having a propylene oxide average degree of polymerization of 5 and an ethylene oxide average degree of polymerization of 105 (PEP-101) or one having a propylene oxide average degree of polymerization of 30 and an ethylene oxide average degree of polymerization of 160 (Pluronic F68), and is most preferably one having a propylene oxide average degree of polymerization of 5 and an ethylene oxide average degree of polymerization of 105. The sucrose fatty acid ester is preferably a stearic acid ester having a hydrophilic-lipophilic balance (HLB) of from 1 to 5, and most preferably one having an HLB of 2 (Surfhope SE PHARMA J-1802). Illustrative examples of sorbitan fatty acid esters include sorbitan monolaurate, sorbitan sesquioleate, sorbitan monostearate and sorbitan monooleate; sorbitan monolaurate is preferred. Illustrative examples of propylene glycol fatty acid esters include propylene glycol dicaprylate, propylene glycol monocaprylate and propylene glycol dicaprate; propylene glycol dicaprylate is preferred. Illustrative examples of $C_{12-22}$ saturated fatty acids include stearic acid, myristic acid and palmitic acid; stearic acid is preferred. One especially preferred combination of emulsifying agents is a combination of PEP-101 with Surfhope SE PHARMA J-1802. Another especially preferred combination of emulsifying agents is a combination of PEP-101 with Surfhope SE PHARMA J-1802 and stearic acid. Yet another especially preferred combination of emulsifying agents is a combination of Pluronic F68 with soy lecithin. An additional especially preferred combination of emulsifying agents is a combination of PEP-101 with sorbitan monolaurate. A further especially preferred combination of emulsifying agents is a combination of PEP-101 with propylene glycol dicaprylate. A still further especially preferred combination of emulsifying agents is a combination of PEP-101 with stearic acid and propylene glycol dicaprylate.

By using the emulsifying agent of the invention, the polyunsaturated fatty acid in the jelly combination is made resistant to oxidation and stably preserved.

Illustrative examples of the gelling agent used in the invention include carrageenan, sodium alginate, guar gum, locust bean gum, tara gum, xanthan gum, cellulose derivatives, carboxyvinyl polymers, carmellose sodium and pullulan. The total content of gelling agents is from 0.01 to 20 wt %, and preferably from 0.1 to 10 wt %. A single gelling agent may be used alone or a plurality of gelling agents may be used together in combination. The gelling agent preferably includes one selected from among carrageenan, locust bean gum, carmellose sodium and pullulan. Each component or the plurality of components is included in an amount of preferably from 0.05 to 10 wt %. The gelling agent more preferably includes carrageenan, locust bean gum, and pullulan and/or carmellose sodium. Each component or the plurality of components is included in an amount of preferably from 0.05 to 10 wt %.

The jelly composition is preferably one which, until it is taken, ensures storage stability, has a good portability and has a suitable jelly strength that enables it to be ingested all at once at the time of administration; and which, after being taken, suitably disintegrates in the oral cavity or the digestive tract, is easy to swallow, and rapidly releases the polyunsaturated fatty acid within the digestive tract. These effects are achievable by using the gelling agent of the present invention.

The releasability of polyunsaturated fatty acids can sometimes be increased by lowering the jelly strength to form an easily disintegrating jelly, although excessively lowering the jelly strength makes it difficult to ingest the jelly as a single bolus. For example, some of the jelly will remain in the filled container or will spill, making it impossible to reliably take the desired amount. On the other hand, excessively increasing the jelly strength will prevent the jelly from readily disintegrating within the oral cavity or the digestive tract when taken, will make it difficult to form the jelly into a bolus of food together with saliva, and will make the jelly difficult to swallow, so that it may even cause aspiration. Therefore, preparing a jelly having an appropriate jelly strength is desirable for obtaining a jelly that is easy to administer.

The jelly strength of the inventive jelly composition is expressed as the value (breaking strength) obtained by dividing the maximum stress (gf) which bears on the plunger by the plunger cross-sectional area ($cm^2$) when measurement is carried out with the following apparatus and under the following conditions.

Apparatus used (rheometer): Texture Analyzer TA-XT-PLUS (manufactured by Stable Micro System Ltd.)
Inside diameter of container filled with jelly composition: 20 mm
Plunger used: cylindrical shape, with 10 mm diameter
Insertion rate: 30 cm/min
Insertion distance: 10 mm
Temperature: room temperature (approx. 25° C.)

In the present invention, "a jelly having an appropriate jelly strength (breaking strength)" refers specifically to a jelly which, for a jelly composition filled into a cylindrical container having an inside diameter of 20 mm, has a jelly strength (breaking strength), obtained by testing with the above apparatus at an insertion distance of 10 mm and room temperature with a 10 mm diameter cylindrical plunger at an insertion rate of 30 cm/min, of at least 50 gf/cm$^2$ but not more than 250 gf/cm$^2$. Such a jelly is an easily administered jelly which has a good portability, and an appropriate jelly strength that enables it to be ingested all at once at the time of administration. When the agar and pectin frequently used to prepare prior-art jelly compositions are used, obtaining an appropriate jelly strength is easy. However, following ingestion, such jellies do not easily disintegrate within the oral cavity and the digestive tract or do not rapidly release polyunsaturated fatty acid within the digestive tract. As a result, it has been confirmed that the absorption of polyunsaturated fatty acids worsens. Thus, preparing a oil-in-water emulsified composition of polyunsaturated fatty acid having the desired function requires the use of at least one gelling agent specified in the present invention.

Combinations of the emulsifying agent and the gelling agent are preferably combinations of an emulsifying agent which includes at least one selected from among polyoxyethylene polyoxypropylene glycols, sucrose fatty acid esters, lecithin, sorbitan fatty acid esters, propylene glycol fatty acid esters and $C_{12-22}$ saturated fatty acids with a gelling agent which includes carrageenan, locust bean gum, pullulan and/or carmellose sodium. Preferred contents of these respective ingredients are 0.5 to 5 wt % of polyoxyethylene polyoxypropylene glycol, 0.1 to 3 wt % of sucrose fatty acid ester, 0.1 to 3 wt % of lecithin, 0.1 to 5 wt % of sorbitan fatty acid ester, 0.1 to 5 wt % of propylene glycol fatty acid ester, 0.1 to 5 wt % of $C_{12-22}$ saturated fatty acid, 0.1 to 2 wt % of carrageenan, 0.05 to 1 wt % of locust bean gum, 0.5 to 5 wt % of pullulan, and 0.1 to 2 wt % of carmellose sodium.

In the practice of the invention, a syneresis inhibitor may be used to suppress syneresis of the jelly composition and ensure long-term stability. Illustrative examples of syneresis inhibitors include carmellose sodium, pullulan, sodium polyacrylate, (hydroxypropyl)methyl cellulose, hydroxypropyl cellulose and microcrystalline cellulose. The syneresis inhibitor content is preferably from 0.01 to 10 wt %, and more preferably from 0.05 to 5 wt %. Below this range, a syneresis inhibiting effect cannot be fully exhibited, whereas above this range, the viscosity during preparation may become too high, making it very difficult to produce a uniform liquid preparation. These syneresis inhibitors may be used singly or as a combination of two or more thereof. Carmellose sodium and/or pullulan are preferred.

In the practice of the invention, a gelling aid may be added for such purposes as to hold down the rise in viscosity of the polyunsaturated fatty acid-containing emulsion in the preparation step, thereby increasing the ease of production and making it easier to fill the composition into individual containers, and also to increase the jelly strength of the cooled jelly composition. Examples of gelling aids that may be used include calcium lactate and potassium chloride. Calcium lactate is preferred. When a gelling aid is added, the content within the jelly composition is typically from 0.01 to 10 wt %, and preferably from 0.1 to 2 wt %.

The jelly composition of the invention may also include, for example, flavoring agents (e.g., sorbitol, erythritol, maltitol, mannitol, xylitol, trehalose), fragrances (e.g., orange oil, peppermint oil, apple flavor), preservatives (e.g., sodium citrate, methyl p-oxybenzoate, propyl p-oxybenzoate), antioxidants (e.g., tocopherol, tocopherol acetate, propyl gallate, ascorbic acid stearate, glycine, sodium ascorbate, sodium erythorbate), emulsifying aids (e.g., concentrated glycerol, macrogol), pH modifiers (e.g., citric acid, acetic acid, phosphoric acid, sodium bicarbonate, sodium hydroxide), buffers, and colorants. These additives are not subject to any particular limitation, provided they are substances commonly used in pharmaceutical and food products. Such additives may be used in suitable combinations. Sorbitol, erythritol, xylitol or trehalose are preferred as the flavoring agent. The amount of flavoring agent included in the jelly composition is preferably from 3 to 30 wt %. An oil-based flavor is preferred as the fragrance, with orange oil being especially preferred. The amount of fragrance included in the jelly composition is preferably from 0.01 to 3 wt %. Concentrated glycerol is preferred as the emulsifying aid. The amount of emulsifying aid included in the jelly composition is preferably from 2 to 20 wt %.

The method of preparing the inventive jelly composition is not subject to any particular limitation. Illustrative, non-limiting, examples of methods for emulsifying the polyunsaturated fatty acid when preparing the inventive jelly composition include mechanical emulsification, phase inversion emulsification, a phase transition method (HLB temperature method) and D-phase emulsification. An example of a method for preparing the inventive jelly composition follows, although the mixing order of the components is not limited to that indicated below. The polyunsaturated fatty acid and the emulsifying agent are thoroughly mixed with a small amount of water, the emulsifying aid and the like, following which these ingredients are uniformly blended with an agitator. The resulting blend is heated and emulsified while adding the prescribed amount of water a little at a time. Next, the gelling agent and, if necessary, a gelling aid are added, after which the mixture is heated and vigorously agitated to form a uniform sol-type composition. This sol-type composition is filled into suitable containers in single-dose amounts, then cooled to form a jelly. The jelly composition containers may be any container, regardless of shape, which can be filled with the jelly composition and for which administration of the composition from the filled container is easy. For example, use can be made of cup-like containers and tube-type containers. Elongated containers formed of a heat-sealable laminated film are preferred in terms of production and also from the standpoint of portability and ease of administration. An especially preferred container is an elongated container which has a gas enclosed on one side thereof and from which, by cutting one end of the laminated film and pushing the gas from both sides, the jelly composition can be forced out all at once. Moreover, because the polyunsaturated fatty acid is prone to oxidation during production, it is desirable to use a container which is not readily permeable to oxygen or to additionally package the container within a packing material that does not allow oxygen to pass through. The amount of jelly composition filled into a single container is preferably from 0.5 to 10 g, and most preferably from 1 to 6 g.

Included among the aspects of the invention is jelly composition packaging wherein the jelly composition manufactured by the above-described method is packaged and held in individual doses within containers.

Also, because polyunsaturated fatty acids are prone to oxidation during production, it is desirable to carry out at least some of the preparation steps in a nitrogen environment, and even more desirable to carry out all of the production steps in a nitrogen environment. By means of preparation in this way under fully controlled production conditions, the peroxide value (POV) of the polyunsaturated fatty acid in the jelly composition immediately after preparation can be set to 10 meq/kg or less. Because polyunsaturated fatty acids readily incur a deterioration in quality due to oxidation and, as a result of such deterioration, take on a distinctive taste and odor, to obtain a jelly composition that is easy to take, it is important that deterioration in the quality of polyunsaturated fatty acids be prevented and that the POV of polyunsaturated fatty acids in the jelly composition during preparation be set to 10 meq/kg or less. Moreover, it is desirable to use deaerated water or deoxygenated water as the water employed when preparing the inventive jelly compositions as doing so enables the POV of polyunsaturated fatty acids within the jelly composition to be held to an even lower level.

Jelly compositions according to the invention are suitable for use as, for example, food products, health foods, health-promoting foods (foods with nutrient function claims, foods for specified health uses), and pharmaceutical products. The inventive jelly compositions are even more suitable for use as oral pharmaceutical products, and are particularly suitable for use in patients having a decreased ability to swallow and patients whose intake of water has been restricted.

Examples according to the invention are given below by way of illustration and should not be construed as limiting the invention.

EXAMPLES

Example 1

A liquid preparation was obtained by weighing out Component A in Table 1, heating it to 80° C. in a nitrogen atmosphere (oxygen concentration, ≤0.2%) to dissolve it, subsequently adding Component B and carrying out emulsification by high-speed agitation, adding Component C and dissolving, then adding Component D. About 3 g each of the liquid preparation was filled into individual packaging containers composed of a laminated film formed into an elongated pouch. The filled containers were then closed by heat-sealing and subsequently cooled, thereby giving a jelly composition containing 20 wt % of ethyl eicosapentaenoate.

TABLE 1

Example 1

| | Component | Content (wt %) |
|---|---|---|
| A | Polyoxyethylene (105) polyoxypropylene (5) glycol | 1.69 |
| | Sucrose fatty acid ester | 0.71 |
| | Concentrated glycerol | 10.00 |
| | Orange oil | 0.90 |
| | Purified water | 15.00 |
| B | Ethyl eicosapentaenoate | 20.00 |
| | 0.01 mol/L Sodium hydroxide | 5.00 |
| | Purified water | as appropriate |
| C | Erythritol | 7.50 |
| | Carrageenan | 0.48 |
| | Locust bean gum | 0.24 |
| | Carmellose sodium | 0.60 |
| D | Calcium lactate | 0.75 |

Example 2

A jelly composition containing 20 wt % of ethyl eicosapentaenoate was prepared by carrying out the same procedure as in Example 1 using the ingredients in Table 2.

TABLE 2

Example 2

| | Component | Content (wt %) |
|---|---|---|
| A | Polyoxyethylene (160) polyoxypropylene (30) glycol | 2.02 |
| | Soy lecithin | 0.38 |
| | Concentrated glycerol | 10.00 |
| | Orange oil | 1.80 |
| | Purified water | 15.00 |
| B | Ethyl eicosapentaenoate | 20.00 |
| | 0.01 mol/L Sodium hydroxide | 5.00 |
| | Purified water | as appropriate |
| C | Xylitol | 20.00 |
| | Carrageenan | 0.45 |
| | Locust bean gum | 0.20 |
| D | Calcium lactate | 0.50 |

Example 3

A jelly composition containing 20 wt % of ethyl eicosapentaenoate was prepared by carrying out the same procedure as in Example 1 using the ingredients in Table 3.

TABLE 3

Example 3

| | Component | Content (wt %) |
|---|---|---|
| A | Polyoxyethylene (160) polyoxypropylene (30) glycol | 2.02 |
| | Soy lecithin | 0.38 |
| | Concentrated glycerol | 10.00 |
| | Macrogol 4000 | 1.50 |
| | Orange oil | 1.80 |
| | Purified water | 15.00 |
| B | Ethyl eicosapentaenoate | 20.00 |
| | 0.01 mol/L Sodium hydroxide | 5.00 |
| | Purified water | as appropriate |
| C | Xylitol | 20.00 |
| | Carrageenan | 0.45 |
| | Locust bean gum | 0.20 |
| D | Calcium lactate | 0.50 |

Example 4

A jelly composition containing 20 wt % of ethyl eicosapentaenoate was prepared by carrying out the same procedure as in Example 1 using the ingredients in Table 4.

TABLE 4

Example 4

| | Component | Content (wt %) |
|---|---|---|
| A | Polyoxyethylene (105) polyoxypropylene (5) glycol | 1.69 |
| | Sucrose fatty acid ester | 0.71 |
| | Concentrated glycerol | 10.00 |
| | Orange oil | 1.80 |
| | Purified water | 15.00 |
| B | Ethyl eicosapentaenoate | 20.00 |
| | 0.01 mol/L Sodium hydroxide | 5.00 |
| | Purified water | as appropriate |
| C | Erythritol | 7.50 |
| | Carrageenan | 0.35 |
| | Locust bean gum | 0.20 |
| | Carmellose sodium | 0.60 |
| D | Calcium lactate | 0.75 |

Example 5

A jelly composition containing 20 wt % of ethyl eicosapentaenoate was prepared by carrying out the same procedure as in Example 1 using the ingredients in Table 5.

TABLE 5

Example 5

| | Component | Content (wt %) |
|---|---|---|
| A | Sucrose fatty acid ester | 0.56 |
| | Polyglycerol fatty acid ester | 1.04 |
| | Concentrated glycerol | 10.00 |
| | Apple flavor | 0.10 |
| | Purified water | 15.00 |
| B | Ethyl eicosapentaenoate | 20.00 |
| | 0.01 mol/L Sodium hydroxide | 5.00 |
| | Purified water | as appropriate |
| C | Xylitol | 10.00 |
| | Carrageenan | 0.45 |
| | Locust bean gum | 0.20 |
| D | Calcium lactate | 0.50 |

Example 6

A jelly composition containing 16 wt % of ethyl eicosapentaenoate was prepared by carrying out the same procedure as in Example 1 using the ingredients in Table 6.

TABLE 6

Example 6

| | Component | Content (wt %) |
|---|---|---|
| A | Polyoxyethylene (105) polyoxypropylene (5) glycol | 1.69 |
| | Sucrose fatty acid ester | 0.71 |
| | Concentrated glycerol | 10.00 |
| | Orange oil | 0.90 |
| | Purified water | 15.00 |
| B | Ethyl eicosapentaenoate | 16.00 |
| | 0.01 mol/L Sodium hydroxide | 5.00 |
| | Purified water | as appropriate |
| C | Erythritol | 7.50 |
| | Carrageenan | 0.48 |
| | Locust bean gum | 0.24 |
| | Carmellose sodium | 0.60 |
| D | Calcium lactate | 0.75 |

Comparative Example 1

About 30 g each of a liquid preparation obtained by carrying out the same procedure as in Example 1 using the ingredients in Table 7 was filled into individual packaging containers composed of a laminated film formed into an elongated pouch. The filled containers were then closed by heat-sealing and subsequently cooled, thereby giving a jelly composition containing 2 wt % of ethyl eicosapentaenoate.

TABLE 7

Comparative Example 1

| | Component | Content (wt %) |
|---|---|---|
| A | Polyglycerol fatty acid ester | 2.00 |
| | Lecithin | 0.38 |
| | Concentrated glycerol | 10.00 |
| | Purified water | 15.00 |
| B | Ethyl eicosapentaenoate | 2.00 |
| | Purified water | as appropriate |

TABLE 7-continued

Comparative Example 1

| | Component | Content (wt %) |
|---|---|---|
| C | Xylitol | 20.00 |
| | Carrageenan | 0.20 |
| | Locust bean gum | 0.07 |
| | Xanthan gum | 0.17 |
| | Guar gum | 0.07 |
| | Powdered arum root (konjak) | 0.40 |
| D | Citric acid | 0.30 |

Comparative Example 2

A jelly composition containing 20 wt % of ethyl eicosapentaenoate was prepared by carrying out the same procedure as in Example 1 using the ingredients in Table 8.

TABLE 8

Comparative Example 2

| | Component | Content (wt %) |
|---|---|---|
| A | Polyoxyethylene (160) polyoxypropylene (30) glycol | 2.02 |
| | Soy lecithin | 0.38 |
| | Concentrated glycerol | 10.00 |
| | Purified water | 15.00 |
| B | Ethyl eicosapentaenoate | 20.00 |
| | Purified water | as appropriate |
| C | Xylitol | 10.00 |
| | Gellan gum | 0.25 |
| | Pectin | 0.25 |
| D | Citric acid | 0.20 |

Test Example 1

The ease of administration and portability of portions of the jelly compositions prepared in Example 1 and in Comparative Example 1 containing 600 mg of ethyl eicosapentaenoate (3 g in Example 1, 30 g in Comparative Example 1) were evaluated by ten volunteers based on questionnaire responses by the volunteers.

TABLE 9

Comparison of ease of administration and portability

| | Example 1 | Comp. Ex. 1 |
|---|---|---|
| Easy to take after a meal | 10 volunteers | 0 volunteers |
| Easy to carry | 10 volunteers | 0 volunteers |

Test Example 2

Referring to a method that is based on the paddle method for elution testing in the Pharmacopoeia of Japan (*International Journal of Pharmaceutics* 95, 67-75), the jelly compositions obtained in Examples 1 to 3 of the invention and the jelly composition obtained in Comparative Example 2 were each tested by placing 200 mL of a sodium phosphate buffer (pH, 6.8; containing 20% of polysorbate 20) as the test solution together with 2,500 polypropylene beads (diameter, 6.35 mm) in a elution testing apparatus beaker, and rotating the paddle at 25 rpm and a temperature of 37° C. The releasability of ethyl eicosapentaenoate from the respective jelly compositions into the test solution was compared.

These results are shown in Table 10 together with the jelly strength measurement results. The jelly strength was measured by the method described above.

TABLE 10

|  | Jelly strength (gf/cm$^2$) | Percent released in 30 minutes |
|---|---|---|
| Example 1 | 152 | 84.3 |
| Example 2 | 54 | 95.6 |
| Example 3 | 63 | 70.2 |
| Comp. Ex. 2 | 150 | 58.2 |

Test Example 3

Figure 1:
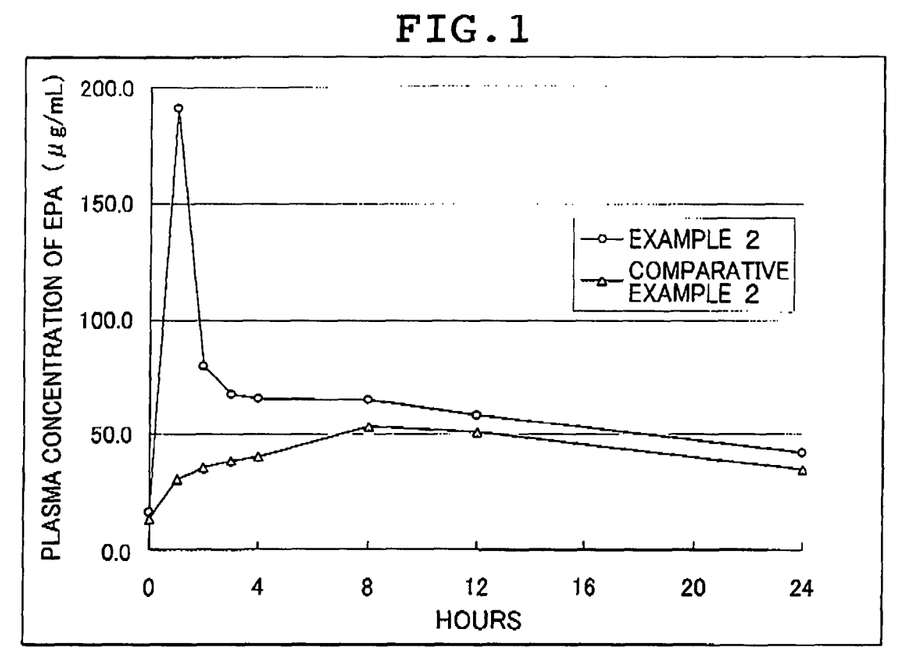
FIG. 1 is a graph showing the change over time in the plasma concentration of EPA in dogs which were orally administered the jelly compositions prepared in Example 2 according to the invention and in Comparative Example 2.

Six beagles were fed softened food, then divided into two groups of three dogs each. The dogs in one group were orally administered the jelly composition prepared in Example 2 and the dogs in the other group were orally administered the jelly composition prepared in Comparative Example 2. In each case, the jelly composition was administered in an amount that contained 900 mg of ethyl eicosapentaenoate. The plasma concentration of EPA in each dog was then measured, and the average values for the two groups were compared. The results are shown in FIG. 1. Substantially no rise in the plasma concentration was observed in Comparative Example 2, whereas a rapid rise in the plasma concentration of EPA was confirmed in Example 2.

Test Example 4

Component A in Table 11 was weighed out, then heated to 80° C. and dissolved. To this was added component B, following which emulsification was carried out by high-speed agitation. Next, Component C (the syneresis inhibitor is shown in Table 12) was added and dissolved, after which Component D was added. The resulting preparation was filled into containers, sealed and cooled, thereby giving jelly compositions containing 20% of ethyl eicosapentaenoate. The jelly strengths and percent syneresis for these jelly compositions are shown in Table 12. "Percent syneresis" refers herein to the value obtained by removing liquid that has exuded from the jelly composition with filter paper, dividing the weight of the exuded liquid as determined from the weight difference before and after removal by the total weight of the jelly composition in the container, and multiplying by 100.

TABLE 11

Examples 7 to 12

|  | Component | Content (wt %) |
|---|---|---|
| A | Polyoxyethylene (160) polyoxypropylene (30) glycol | 2.02 |
|  | Soy lecithin | 0.38 |
|  | Concentrated glycerol | 10.00 |
|  | Orange oil | 1.80 |
|  | Purified water | 15.00 |
| B | Ethyl eicosapentaenoate | 20.00 |
|  | 0.01 mol/L Sodium hydroxide | 5.00 |
|  | Purified water | as appropriate |
| C | Xylitol | 20.00 |
|  | Carrageenan | 0.45 |
|  | Locust bean gum | 0.20 |
|  | Syneresis inhibitor | prescribed amount |
| D | Calcium lactate | 0.50 |

TABLE 12

Examples 7 to 12

|  | Syneresis inhibitor | Jelly strength (gf/cm$^2$) | Percent syneresis |
|---|---|---|---|
| Example 7 | Carmellose sodium, 0.6% | 198 | 1.3 |
| Example 8 | Pullulan, 1% | 227 | 2.3 |
| Example 9 | Sodium polyacrylate, 0.05% | 232 | 4.5 |
| Example 10 | (Hydroxypropyl)methyl cellulose, 1% | 194 | 4.2 |
| Example 11 | Hydroxypropyl cellulose, 1% | 220 | 3.5 |
| Example 12 | Microcrystalline cellulose, 1% | 221 | 4.6 |

Example 13

Component A in Table 13 was weighed out, then heated to 80° C. and dissolved in a nitrogen atmosphere (oxygen concentration, ≤0.2%). Component B was added thereto and emulsification was carried out by high-speed agitation, following which Component C was added and dissolved, thereby forming a liquid preparation. The liquid preparation was then subjected to the same operations as in Example 1, giving a jelly composition containing 20 wt % of ethyl eicosapentaenoate.

TABLE 13

Example 13

|  | Component | Content (wt %) |
|---|---|---|
| A | Polyoxyethylene (105) polyoxypropylene (5) glycol | 1.00 |
|  | Sorbitan monolaurate | 1.00 |
|  | Concentrated glycerol | 7.50 |
|  | Ascorbic acid stearate | 0.02 |
|  | Sodium erythorbate | 1.30 |
|  | Orange oil | 0.90 |
|  | Purified water | 15.00 |
| B | Ethyl eicosapentaenoate | 20.00 |
|  | Sodium hydroxide | as appropriate |
|  | Purified water | as appropriate |
| C | Trehalose | 15.00 |
|  | Carrageenan | 0.42 |
|  | Locust bean gum | 0.25 |
|  | Pullulan | 3.00 |

Example 14

A jelly composition containing 20 wt % of ethyl eicosapentaenoate was prepared by carrying out the same procedure as in Example 13 using the ingredients in Table 14.

TABLE 14

Example 14

|  | Component | Content (wt %) |
|---|---|---|
| A | Polyoxyethylene (105) polyoxypropylene (5) glycol | 1.13 |
|  | Sucrose fatty acid ester | 0.47 |
|  | Stearic acid | 1.00 |
|  | Concentrated glycerol | 7.50 |
|  | Ascorbic acid stearate | 0.02 |
|  | Sodium erythorbate | 1.30 |
|  | Orange oil | 0.90 |
|  | Purified water | 15.00 |
| B | Ethyl eicosapentaenoate | 20.00 |
|  | Sodium hydroxide | as appropriate |
|  | Purified water | as appropriate |
| C | Trehalose | 15.00 |
|  | Carrageenan | 0.42 |

TABLE 14-continued

Example 14

| Component | Content (wt %) |
| --- | --- |
| Locust bean gum | 0.25 |
| Pullulan | 3.00 |

Example 15

A jelly composition containing 20 wt % of ethyl eicosapentaenoate was prepared by carrying out the same procedure as in Example 13 using the ingredients in Table 15.

TABLE 15

Example 15

| | Component | Content (wt %) |
| --- | --- | --- |
| A | Polyoxyethylene (105) polyoxypropylene (5) glycol | 1.53 |
| | Propylene glycol dicaprylate | 0.87 |
| | Concentrated glycerol | 7.50 |
| | Ascorbic acid stearate | 0.02 |
| | Sodium erythorbate | 1.30 |
| | Orange oil | 0.90 |
| | Purified water | 15.00 |
| B | Ethyl eicosapentaenoate | 20.00 |
| | Sodium hydroxide | as appropriate |
| | Purified water | as appropriate |
| C | Trehalose | 15.00 |
| | Carrageenan | 0.42 |
| | Locust bean gum | 0.25 |
| | Pullulan | 3.00 |

Example 16

A jelly composition containing 20 wt % of ethyl eicosapentaenoate was prepared by carrying out the same procedure as in Example 13 using the ingredients in Table 16.

TABLE 16

Example 16

| | Component | Content (wt %) |
| --- | --- | --- |
| A | Polyoxyethylene (105) polyoxypropylene (5) glycol | 1.60 |
| | Concentrated glycerol | 7.50 |
| | Ascorbic acid stearate | 0.02 |
| | Sodium erythorbate | 1.30 |
| | Orange oil | 0.90 |
| | Purified water | 15.00 |
| B | Ethyl eicosapentaenoate | 20.00 |
| | Sodium hydroxide | as appropriate |
| | Purified water | as appropriate |
| C | Trehalose | 15.00 |
| | Carrageenan | 0.42 |
| | Locust bean gum | 0.25 |
| | Pullulan | 3.00 |

Example 17

A jelly composition containing 20 wt % of ethyl eicosapentaenoate was prepared by carrying out the same procedure as in Example 13 using the ingredients in Table 17.

TABLE 17

Example 17

| | Component | Content (wt %) |
| --- | --- | --- |
| A | Polyoxyethylene (105) polyoxypropylene (5) glycol | 1.53 |
| | Propylene glycol dicaprylate | 0.87 |
| | Stearic acid | 0.50 |
| | Concentrated glycerol | 7.50 |
| | Ascorbic acid stearate | 0.02 |
| | Sodium erythorbate | 1.30 |
| | Orange oil | 0.90 |
| | Purified water | 15.00 |
| B | Ethyl eicosapentaenoate | 20.00 |
| | Sodium hydroxide | as appropriate |
| | Purified water | as appropriate |
| C | Trehalose | 15.00 |
| | Carrageenan | 0.42 |
| | Locust bean gum | 0.25 |
| | Pullulan | 3.00 |

Example 18

A jelly composition containing 30 wt % of ethyl eicosapentaenoate was prepared by carrying out the same procedure as in Example 13 using the ingredients in Table 18.

TABLE 18

Example 18

| | Component | Content (wt %) |
| --- | --- | --- |
| A | Polyoxyethylene (105) polyoxypropylene (5) glycol | 2.02 |
| | Sucrose fatty acid ester | 0.84 |
| | Concentrated glycerol | 7.50 |
| | Ascorbic acid stearate | 0.02 |
| | Sodium erythorbate | 1.30 |
| | Orange oil | 0.90 |
| | Purified water | 15.00 |
| B | Ethyl eicosapentaenoate | 30.00 |
| | Sodium hydroxide | as appropriate |
| | Purified water | as appropriate |
| C | Trehalose | 7.50 |
| | Carrageenan | 0.49 |
| | Locust bean gum | 0.25 |
| | Pullulan | 1.5 |

Test Example 5

For each of the jelly compositions in Examples 1 to 4 of the invention, 1 g of the composition was weighed, following which sodium phosphate buffer was added and uniformly dispersed. Chloroform was then added to the dispersion, causing ethyl eicosapentaenoate to be extracted therein. The peroxide value (POV) of the polyunsaturated fatty acid in the jelly composition was determined by the Standard Fats and Oils Test Method (Japan Oil Chemists' Society) for the extracted ethyl eicosapentaenoate. The results are shown in Table 19 below.

TABLE 19

| | POV (meq/kg) |
| --- | --- |
| Example 1 | 1.37 |
| Example 2 | 3.48 |
| Example 3 | 4.41 |
| Example 4 | 4.90 |

Test Example 6

Referring to a method that is based on the paddle method for elution testing in the Pharmacopoeia of Japan (*International Journal of Pharmaceutics* 95, 67-75), the jelly compositions obtained in Examples 13 to 17 of the invention were each tested by placing 160 mL of an artificial gastric fluid (a solution prepared by adjusting an aqueous solution containing 115 mmol/L of sodium chloride and 35 mmol/L of potassium chloride to pH 2.5 with hydrochloric acid) as the test solution together with 2,000 nylon beads (diameter, 6.4 mm) in a elution testing apparatus beaker, rotating the paddle at 25 rpm and a temperature of 37° C. The releasability of ethyl eicosapentaenoate from the respective jelly compositions into the test solution was compared. These results are shown in Table 20 together with the jelly strength measurement results. The jelly strength was measured by the method described above.

TABLE 20

|  | Jelly strength (gf/cm$^2$) | Percent released in 30 minutes |
| --- | --- | --- |
| Example 13 | 118 | 89.4 |
| Example 14 | 113 | 57.3 |
| Example 15 | 148 | 67.4 |
| Example 16 | 126 | 79.8 |
| Example 17 | 115 | 79.4 |

Test Example 7

Figure 2:
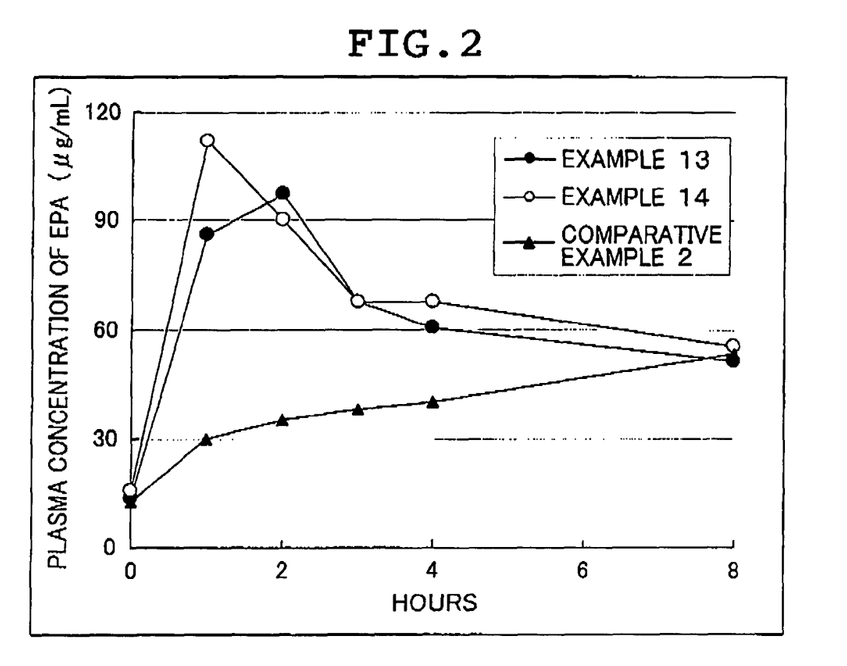
FIG. 2 is a graph showing the change over time in the plasma concentration of EPA in dogs which were orally administered the jelly compositions prepared in Examples 13 and 14 according to the invention and in Comparative Example 2.

Six to eight beagles were fed softened food, then divided into two groups. The jelly compositions of Examples 13 and 14 according to the invention and the jelly composition of Comparative Example 2 were orally administered (in amounts containing 600 mg of EPA-E in Examples 13 and 14, and in an amount containing 900 mg of EPA-E in Comparative Example 2). The plasma concentrations of EPA were measured and the average values for each group were compared. The results are shown in FIG. 2. Substantially no rise in the plasma concentration was observed in Comparative Example 2, whereas a rapid rise in the plasma concentration of EPA was confirmed in Examples 13 and 14 due to good absorption of the active ingredient. These findings confirmed that the jelly compositions-according to the present invention have better properties as pharmaceutical compositions than the jelly composition of the comparative example.

The invention claimed is:

1. An easy-release jelly pharmaceutical composition comprising:
at least one emulsified pharmaceutical component selected from the group consisting of eicosapentaenoic acid, docosahexaenoic acid and ethyl esters thereof, wherein said at least one pharmaceutical component is in an amount greater than 10 wt %;
an emulsifying agent which is at least one selected from the group consisting of polyoxyethylene polyoxypropylene glycols, sucrose fatty acid esters, lecithin, polyglycerol fatty acid esters, glycerol fatty acid esters, sorbitan fatty acid esters, propylene glycol fatty acid esters and $C_{12-22}$ saturated fatty acids, the emulsifying agent being in an amount of 0.01-10 wt %;
a gelling agent which is at least one selected from the group consisting of 0.1-2 wt % of carrageenan and 0.05-1 wt % of locust bean gum;
a syneresis inhibitor in an amount of 0.05-5 wt % which is at least one selected from the group consisting carmellose sodium and pullulan; and
a flavoring agent in an amount of 3-20 wt % selected from the group consisting of erythritol, xylitol, and trehalose;
wherein the easy-release jelly pharmaceutical composition is capable of being orally ingested, and when filled into a cylindrical container having an inside diameter of 20 mm, has a jelly strength (breaking strength) of at least 50 gf/cm$^2$, but not more than 250 gf/cm$^2$, obtained by testing with a rheometer using a 10-mm diameter cylindrical plunger at an insertion rate of 30 cm/min, an insertion distance of 10 mm and room temperature, and
wherein said easy-release jelly pharmaceutical composition has a release ratio of at least 50% of the pharmaceutical component into a test solution containing 2000 nylon beads having a diameter of 6.4 mm, 30 minutes after mixing the easy-release jelly pharmaceutical composition into the test solution and stirring at a temperature of 37° C. with a paddle rotation at 25 rpm, said test solution being composed of 160 mL of an artificial gastric fluid comprising an aqueous solution containing 115 mmol/L of sodium chloride and 35 mmol/L of potassium chloride adjusted with hydrochloric acid to a pH of 2.5.

2. The easy-release jelly pharmaceutical composition of claim 1, said composition as the gelling agent carrageenan and locust bean gum and additionally comprising at least one selected from the group consisting of fragrances, preservatives, antioxidants, gelling aids, emulsifying aids and pH modifiers.

3. An easy-release jelly composition comprising a pharmaceutical component selected from the group consisting of eicosapentaenoic acid, docosahexaenoic acid and ethyl esters thereof in an amount greater than 10 wt %;
at least one emulsifying agent selected from the group consisting of polyoxyethylene polyoxypropylene glycols, sucrose fatty acid esters, lecithin, polyglycerol fatty acid esters, glycerol fatty acid esters, sorbitan fatty acid esters, propylene glycol fatty acid esters and $C_{12-22}$ saturated fatty acids, the emulsifying agent being in an amount of 0.01-10 wt %;
a gelling agent including 0.1-2 wt % of carrageenan and 0.05-1 wt % of locust bean gum, and;
a syneresis inhibitor in an amount of 0.05-5 wt % which is at least one selected from the group consisting carmellose sodium and pullulan; and
a flavoring agent in an amount of 3-20 wt % selected from the group consisting of erythritol, xylitol, and trehalose,
wherein the easy-release jelly pharmaceutical composition is capable of being orally ingested, and when filled into a cylindrical container having an inside diameter of 20 mm, has a jelly strength (breaking strength) of at least 50 gf/cm$^2$, but not more than 250 gf/cm$^2$, obtained by testing with a rheometer using a 10-mm diameter cylindrical plunger at an insertion rate of 30 cm/min, an insertion distance of 10 mm and room temperature, and
wherein said easy-release jelly pharmaceutical composition has a release ratio of at least 50% of the pharmaceutical component into a test solution containing 2000 nylon beads having a diameter of 6.4 mm, 30 minutes after mixing the easy-release jelly pharmaceutical composition into the test solution and stirring at a temperature of 37° C. with a paddle rotation at 25 rpm, said test solution being composed of 160 mL of an artificial gastric fluid comprising an aqueous solution containing 115 mmol/L of sodium chloride and 35 mmol/L of potassium chloride adjusted with hydrochloric acid to a pH of 2.5.

4. A process for manufacturing the easy-release jelly pharmaceutical composition of claim 1, which includes the emulsified pharmaceutical component selected from the group consisting of eicosapentaenoic acid, docosahexaenoic acid and ethyl esters thereof in an amount greater than 10 wt %, the process comprising the steps of, in order,
- rendering the pharmaceutical component, an aqueous solvent, and the emulsifying agent into an oil-in-water emulsion;
- adding the gelling agent and the syneresis inhibitor to the emulsion to form a sol composition; and
- cooling the sol composition, and wherein the easy-release jelly composition comprises between 3 and 20 wt % of at least one flavoring agent selected from erythritol, xylitol, and trehalose, wherein said composition has a jelly consistency.

5. The process of claim 4, wherein the sol composition that has been formed is filled into individual-dose packaging, the respective manufacturing process steps and the filling step are carried out in a nitrogen atmosphere, and the pharmaceutical component in the jelly composition has a peroxide value (POV) just after filling of not more than 10 meq/kg.

6. A jelly composition packaging comprising the easy-release jelly pharmaceutical composition manufactured by the method of claim 5 and packaged in individual doses.

7. The easy-release jelly pharmaceutical composition of claim 1, wherein the easy release is defined as when 200 mL of a sodium phosphate buffer (pH of 6.8; containing 20% of polysorbate 20) is used as the test solution, 2,500 polypropylene beads (diameter of 6.35 mm) are placed together with the test solution in a dissolution testing apparatus beaker, and testing is carried out by rotating the paddle at 25 rpm and a temperature of 37° C., at least 65% (percent release) of the pharmaceutical component is released into the test solution at 30 minutes following the start of the test.

8. The easy-release jelly pharmaceutical composition of claim 1, wherein the pharmaceutical component is ethyl eicosapentaenoate, ethyl docosahexaenoate or a mixture thereof.

9. The easy-release jelly composition of claim 3, wherein the composition comprises 0.1 to 2 wt % of carmellose sodium.

10. The easy-release jelly composition of claim 3, wherein the easy release is defined as when 200 mL of a sodium phosphate buffer (pH of 6.8; containing 20% of polysorbate 20) is used as the test solution, 2,500 polypropylene beads (diameter of 6.35 mm) are placed together with the test solution in a dissolution testing apparatus beaker, and testing is carried out by rotating the paddle at 25 rpm and a temperature of 37° C., at least 65% (percent release) of the pharmaceutical component is released into the test solution at 30 minutes following the start of the test.

11. The easy-release jelly pharmaceutical composition of claim 1, wherein the syneresis inhibitor is pullulan.

12. The easy-release jelly composition of claim 3, wherein the syneresis inhibitor is pullulan.

13. The process of claim 4, wherein the syneresis inhibitor is pullulan.

14. The easy-release jelly pharmaceutical composition of claim 1, further comprising an antioxidant, wherein the antioxidant comprises at least one of tocopherol, tocopherol acetate, propyl gallate, ascorbic acid stearate, glycine, sodium ascorbate, and sodium erythorbate.

15. The easy-release jelly composition of claim 3, further comprising an antioxidant, wherein the antioxidant comprises at least one of tocopherol, tocopherol acetate, propyl gallate, ascorbic acid stearate, glycine, sodium ascorbate, and sodium erythorbate.

16. The easy-release jelly pharmaceutical composition of claim 1, said composition comprising greater than 15 wt % of the pharmaceutical component.

17. The easy-release jelly composition of claim 3, said composition comprising greater than 15 wt % of the pharmaceutical component.

18. The easy-release jelly pharmaceutical composition of claim 1, said composition comprising 20 wt % or more of the pharmaceutical component.

19. The easy-release jelly composition of claim 3, said composition comprising 20 wt % or more of the pharmaceutical component.

20. The easy-release jelly composition of claim 4, wherein:
 (i) said syneresis inhibitor is carmellose sodium and/or pullulan, and
 (ii) said flavoring agent is erythritol, xylitol and/or trehalose.

21. The easy-release jelly pharmaceutical composition of claim 3, said composition as the gelling agent carrageenan and locust bean gum and additionally comprising at least one selected from the group consisting of fragrances, preservatives, antioxidants, gelling aids, emulsifying aids and pH modifiers.

22. The easy-release jelly pharmaceutical composition of claim 3, wherein the pharmaceutical component is ethyl eicosapentaenoate, ethyl docosahexaenoate or a mixture thereof.

* * * * *